United States Patent [19]

Ahlbeck

[11] 4,421,510
[45] Dec. 20, 1983

[54] URINE DRAINAGE DEVICE PERMITTING TRAINING OF THE BLADDER

[76] Inventor: Stig G. Ahlbeck, Västanväg 28, S-213 16 Malmö, Sweden

[21] Appl. No.: 204,371
[22] PCT Filed: Jan. 17, 1980
[86] PCT No.: PCT/SE80/00013
§ 371 Date: Sep. 18, 1980
§ 102(e) Date: Sep. 18, 1980
[87] PCT Pub. No.: WO80/01454
PCT Pub. Date: Jul. 24, 1980

[51] Int. Cl.³ .............................................. A61M 1/00
[52] U.S. Cl. ............................... 604/323; 137/513.3; 137/513.5; 137/859
[58] Field of Search ................. 137/859, 513.3, 513.5, 137/513.7; 128/294, 295, 274, 760, 766, 205.24; 271/117; 604/323, 335, 350

[56] References Cited

U.S. PATENT DOCUMENTS

| | | | |
|---|---|---|---|
| 2,585,863 | 2/1952 | Smith | 137/53 |
| 2,758,609 | 8/1956 | Dickert et al. | 137/859 |
| 3,606,871 | 9/1971 | Gropp et al. | 137/513.7 |
| 3,626,980 | 12/1971 | Svensson | 128/295 |
| 3,768,102 | 10/1973 | Kwan-Gett et al. | 3/1 |
| 3,933,171 | 1/1976 | Hay | 128/205.24 |
| 4,193,403 | 3/1980 | Langston et al. | 128/295 |
| 4,241,756 | 12/1980 | Bennett et al. | 137/859 |

FOREIGN PATENT DOCUMENTS

| | | | |
|---|---|---|---|
| 990166 | 6/1972 | Canada | 128/295 |
| 389803 | 11/1976 | Sweden | |
| 1066539 | 4/1967 | United Kingdom | |

Primary Examiner—John D. Yasko
Assistant Examiner—J. L. Kruter
Attorney, Agent, or Firm—Saidman, Sterne & Kessler

[57] ABSTRACT

A urine drainage device which provides reliable and effective bladder training is disclosed for use with a catheter connectable to the bladder and communicating with a collection bag. The device comprises a valve for controlling the connection between the catheter and the collection bag. The valve includes a normally closed inlet which is opened when a predetermined bladder fluid pressure is reached. A pressure substantially below the opening pressure of the valve is capable of maintaining the inlet in an open condition.

11 Claims, 2 Drawing Figures

URINE DRAINAGE DEVICE PERMITTING TRAINING OF THE BLADDER

BACKGROUND OF THE INVENTION

This invention relates to a urine drainage device permitting training of the bladder and comprising a catheter connectable to the bladder and communicating with a collection bag.

In the treatment of patients suffering from urine incontinence it is of great importance that the normal function of the bladder be re-established if possible, e.g. subsequent to a disease which has interfered with the normal function of the bladder. If the bladder is not allowed to expand by accumulating urine, there is a great risk of the bladder being shrunk, which means tht the normal function of the bladder can never be re-established. This in turn means that the ability of the bladder to accumulate urine is almost completely lost and that the urine has to be continuously drained to a collection bag e.g. by means of a catheter.

Especially in geriatric hospital treatment, incontinence pads are widely used and recently disposable incontinent diapers as well. This treatment of the incontinent patients imposes strain on the nursing staff involved because it is necessary repeatedly to change the incontinence pads or diapers in order to achieve humane treatment of these patients. Even if the normal function of the bladder can never be re-established due to age or other reasons, it is of great importance that the accumulating ability of the bladder be maintained to relieve the strain imposed on the nursing staff, because the discharge of urine then could be fairly well controlled.

Devices of several different types for use in connection with bladder-training of incontinent patients have been suggested. The Swedish patent specification 389,803 discloses one type of such device. This device requires, as most existing devices for bladder-training do, the use of a catheter usually connected to a urine collection bag. Devices are also known which are provided with a pressure sensing system for controlling the clamping of the catheter which is clamped until a predetermined pressure is reached in the bladder/catheter, the catheter then being relieved to allow drainage of the bladder.

None of these prior art devices meets reasonable requirements concerning a simple and reliable function; they are complicated as to construction and handling.

OBJECTS OF THE INVENTION

It is a primary object of this invention to provide a urine drainage device which is extremely simple and reliable and which allows an effective bladder-training on patients confined to bed as well as other patients.

It is a further object of this invention to provide a urine drainage device for permitting automatic drainage of the bladder when a predetermined maximum pressure in the bladder has been reached.

A still further object of this invention is to provide a urine drainage device which simultaneously forms a bacteriological barrier, i.e. prevents urine back flow from the urine drainage device to the bladder.

Yet another object of this invention is to provide a urine drainage device for allowing automatic drainage of the bladder at a pre-set maximum pressure or upon accumulating a predetermined amount of urine in the bladder.

Another object of this invention is to provide a urine drainage device comprising few movable parts, the handling and using of which do not require much attention from the nursing staff and which in many cases can be operated by the patient himself.

A still further object of this invention is to provide a urine drainage device which may well be used also by patients whose normal bladder function will never be regained, the normal function of the bladder being imitated by using or maintaining the maximum capacity of the patient's bladder, i.e. the ability thereof to accumulate urine.

SUMMARY OF THE INVENTION

To achieve the foregoing objects and in accordance with the purpose of the invention, as embodied and broadly described herein, the urine drainage device according to the invention comprises a valve for controlling a connection between a catheter and a collection bag, the valve including an inlet connected to the catheter, an outlet connected to the collection bag, and a valve body for controlling the connection between the inlet and the outlet, the valve body being arranged to keep the inlet closed by a resilient force and to open the inlet when a predetermined pressure is reached in the inlet, and being arranged at the inlet such that a pressure in the inlet substantially below the opening pressure of the valve is capable of keeping the valve body in the opened position until the resilient force exceeds the force acting on the valve body and provided by the fluid pressure in the inlet.

The resilient force acting on the valve body can be obtained by using a valve in which the valve body proper is arranged as a cup spring (Belleville spring), e.g. as disclosed in U.S. Pat. No. 2,585,863, wherein the valve body has a flat characteristic and provides a certain resetting force towards the inlet when the valve body is in the open position thereof.

It is of course possible to arrange the valve body as a piston, the resilient force of which is provided by means of mechanical spring means, only part of the piston area being exposed to the inlet pressure of the valve when the valve is in a closed position.

Other arrangements of the valve are possible. Thus, a resilient diaphragm can be arranged to contact and cover the inlet resiliently, whereby a further resilient force towards the inlet is applied on the diaphragm.

However, in a preferred embodiment of the invention only one movable element is used in the valve. Such an element forms the valve body and comprises a resilient diaphragm partially defining a chamber into which the outlet opens, the diaphragm contacting a sealing bead surrounding the inlet to form a fluid tight seal below a certain maximum fluid pressure in the inlet.

The valve constituting part of the urine drainage device preferably comprises a circular valve housing in which the inlet is arranged centrally and which defines together with the diaphragm the chamber into which the outlet opens. The diaphragm is tightened over the valve housing to contact resiliently the sealing bead surrounding the opening of the inlet to the chamber.

An increase in the resilient force acting against the inlet can be achieved by arranging peripheral screw threads or grooves on the circular valve housing together with a lid formed with co-operating screw threads or shoulders engaging the housing, provided that the peripheral edge portion of the resilient diaphragm engages the lid in such a way that the diaphragm is tightened when the lid is screwed onto the valve housing.

Preferably, fastening means integral with the valve housing is used to secure the valve to the patient's body by anchoring bands or directly to the clothes of the patient by safety-pins or the like.

BRIEF DESCRIPTION OF THE DRAWINGS

The accompanying drawing illustrates one embodiment of the invention showing the simplest variant of the valve wherein a single movable element is provided, and together with the description serves to explain the principles of the invention In the drawing.

DETAILED DESCRIPTION OF THE PREFERRED EMBODIMENT

Figure 1:
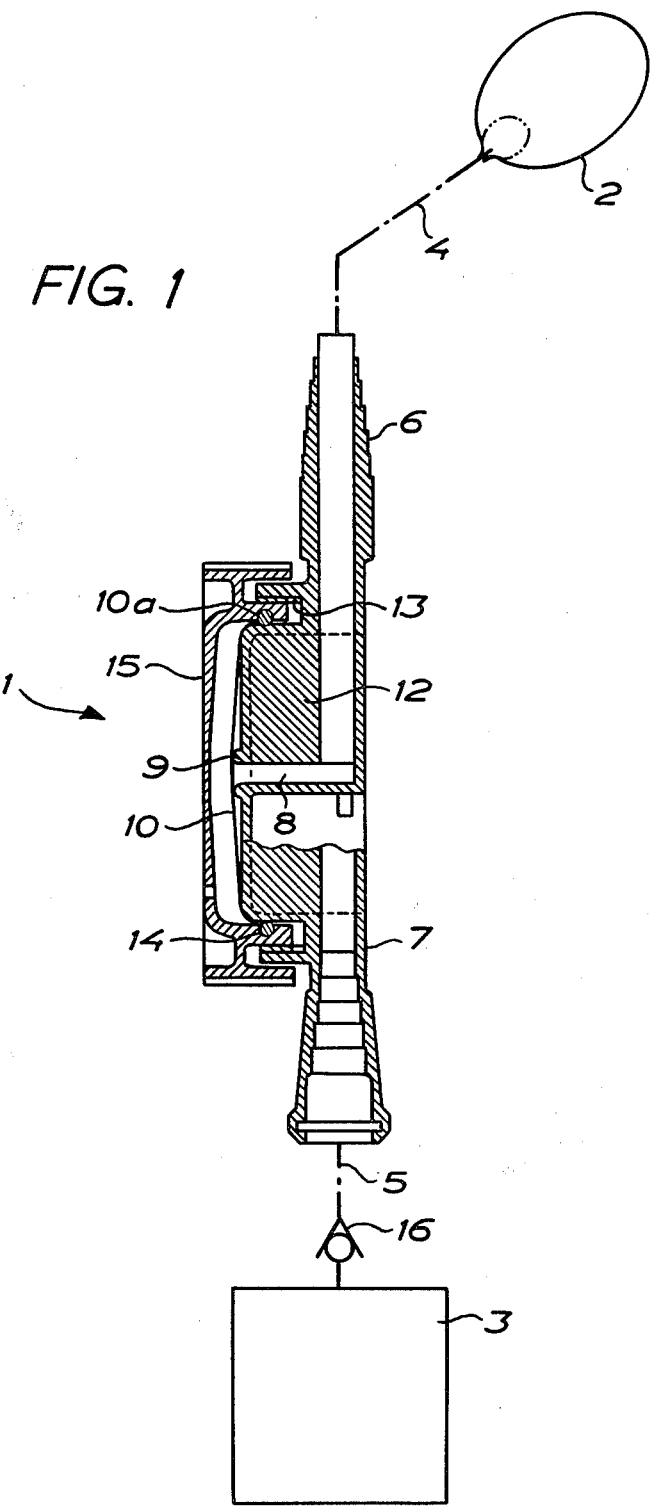
FIG. 1 is an axial cross sectional view of a valve connected to a catheter and a collection bag.
Figure 2:
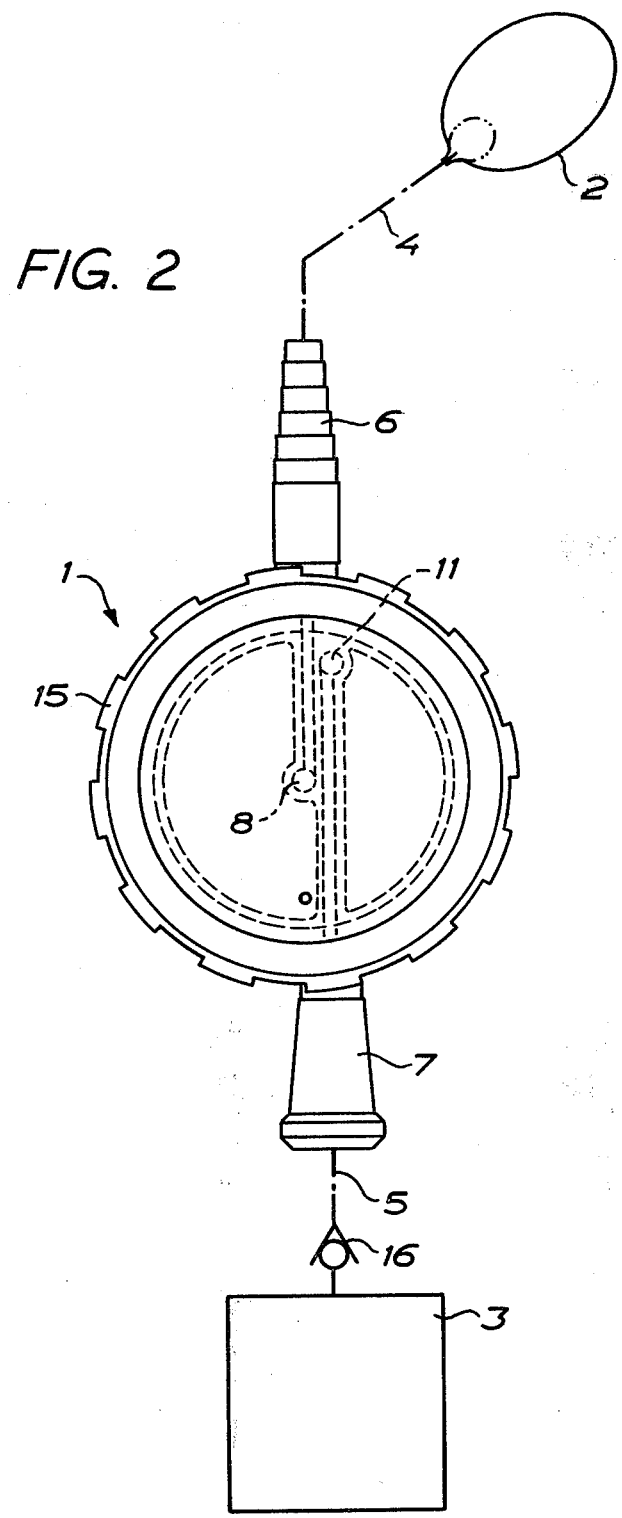
FIG. 2 is an elevational view of the valve shown in FIG. 1.

The urine drainage device according to the invention comprises a valve 1 connected between a bladder 2 and a collection bag 3 through a connection 6 and a catheter 4, and a connection 7 and a conduit 5, respectively.

The valve 1 comprises a circular valve housing 12 provided with internal screw threads 13 co-operating with external screw threads on a circular lid 15. In the lid 15 an internal peripheral groove 14 is provided, into which a bead-formed peripheral edge portion 10a of a diaphragm 10 is engaged. Thus, rotation of the lid 15 on valve housing 12 effects the tightening of the diaphragm 10 onto the valve housing. In the valve housing there is an inlet 8 and an oulet 11. An annular sealing bead 9 surrounds the opening of the inlet 8. The lid 15 may be partially perforated, but in any case must protect the diaphragm 10 against external influence which may cause malfunction of the valve.

Urine is drained to the conduit 6 and the inlet 8 through the catheter 4, and will exert a pressure in the inlet 8. Since the resilient diaphragm 10 resiliently contacts the sealing bead 9, the inlet 8 is closed, but when the fluid pressure in the inlet 8 reaches a certain level which is able to exert a force on the portion of the diaphragm 10 surrounded by the sealing bead g, and which exceeds the bearing force of the diaphragm, the diaphragm 10 will be lifted away from the sealing bead 9. In this position of the diaphragm, the area of the diaphragm exposed to the fluid pressure will be large as compared with the area of the diaphragm surrounded by the sealing bead 9, which means that the resulting force exerted by the fluid pressure on the diaphragm will keep the diaphragm away from the sealing bead even when the fluid pressure in the inlet 8 decreases during drainage of the bladder.

The outlet 11 is necessarily located above the inlet 8 to evacuate the air in the chamber when a fluid flow through the valve 1 is initiated. A fluid flow connection is established between the inlet 8 and the outlet 11 of the valve 1 as long as the pressure in the inlet 8 is sufficient to exert a force on the diaphragm which exceeds the counteracting force exerted by the diaphragm. When the fluid pressure acting on the major area of the diaphragm has decreased to a certain level, the diaphragm returns by resiliency to a position where it co-operates again with the sealing bead 9 to form a fluid tight seal. Thereupon, the connection between the inlet and the outlet of the valve will be interrupted.

The opening pressure and the closing pressure of the valve may be varied within wide limits by suitable choice of the resiliency of the diaphragm material and, above all, by dimensioning the areas of the diaphragm exposed to fluid pressure, i.e. on one hand, the area surrounded by the sealing bead 9, and, on the other hand, the total area of the diaphragm exposed to fluid pressure when the valve is in its open position. In the disclosed embodiment of the invention, the latter area comprises a circular area, the diameter of which corresponds substantially to the diameter of the valve housing 12.

Axial adjustment of the lid 15 over the valve housing 12 means that the bearing pressure of the diaphragm exerted on the sealing bead 9 will be increased. Thus, this means that an increased fluid pressure must be reached to the inlet 8 in order to exert a force sufficient to lift the diaphragm from the sealing bead 9. An incontinent patient using the urine drainage device of this invention will recognize a need to urinate, since the muscles controlling the bladder will be influenced during the continuous accumulation of urine in the bladder in the amount sufficient to create a predetermined fluid pressure in the inlet of the valve prior to the automatic opening of the valve. When this need becomes too urgent, the patient may create a strain and thereby further increase the pressure onto the bladder. This increased pressure may be enough to allow the opening of the valve. Thus, ingenious eneuresis may be imitated to a great extent by a patient using the urine drainage device of this invention.

The need for rinsing the bladder may not be necessary when using the urine drainage device of this invention. Today it is often necessary to rinse the bladder when the urine is continously drained from the bladder, i.e. when the muscles normally controlling the bladder are not stimulated.

The reduced need for rinsing the bladder can be explained by the fact that the valve 1 permits an extraordinarily rapid movement of the diaphragm 10 away from the sealing bead 9, which means that the existing maximum fluid pressure within the bladder creates an initial turbulent fluid flow out of the bladder. Such turbulent fluid flow sustains the evacuation of heavy urine products from the bladder, including such urine products as exist below the outlet of the catheter 4 inserted into the bladder 2.

Preferably, the lid 15 of the valve is provided with, e.g., three distinct setting positions, which may be indicated by symbols: one for use in bed; one for use when the patient is allowed to move in an upright position; and one creating a further increased opening pressure on the valve which may be necessary to prevent a premature discharge of urine if the patient is suffering from coughing. When the patient coughs, this can result in an increased pressure in the abdominal cavity creating an unintended pressure on the bladder which may be, sufficient to open the valve.

To prevent a back flow of urine i.e. from the collection bag 3 to the bladder 2, which may occur when an external pressure is exerted onto the bag, a check valve 16 is preferably arranged between the outlet 11 of the valve 1 and the inlet of the bag 3.

It will be apparent to those skilled in the art that various other modifications and variations in addition to those mentioned above could be made in the urine drainage device of the invention without departing from the scope and spirit of the invention.

Thus, it is possible to arrange the resilient diaphragm in a stationary position around the periphery of the valve housing and to produce a constant bearing pressure against the sealing bead, which pressure can be exceeded by a low fluid pressure in the inlet of the valve. The diaphragm is arranged to be retained in its closed position against the sealing bead by exerting an external force on the diaphragm, which force can be produced by mechanical spring means arranged inside the lid. This external force may be transferred to the diaphragm via a stiffened portion of the diaphragm. Setting the opening pressure of the valve may easily be selected by using the co-operating threads of the valve housing and the lid, respectively. Preferably, the mechanical spring means is integral with the lid.

I claim:

1. For use in a urine drainage device which includes a catheter insertable into a bladder and a collection bag in fluid communication with the catheter, a valve for bladder control adapted to be interposed to the fluid communication path between the catheter and the collection bag, said valve comprising:
   (i) a housing having an inlet adapted to communicate with the bladder and an outlet adapted to communicate with the collection bag;
   (ii) a closure element mounted to said housing; and
   (iii) means for pulling said closure element taut over said inlet to resiliently seal said inlet, said closure element being movable between a first position in which said inlet is closed by said closure element and a second position in which said inlet and said outlet are in fluid communication, wherein said closure element has a first fluid contacting surface area responsive to fluid pressure in the bladder when in said first position and a second fluid contacting surface area responsive to fluid pressure in the bladder when in said second position, said second fluid contacting surface area being substantially greater than said first fluid contacting surface area, such that the bladder fluid pressure required to maintain said closure element in said second position is substantially less than the bladder fluid pressure required to move said closure element from said first position to said second position.

2. The valve of claim 1, further comprising means to adjust the resiliency of said closure element to change the fluid pressure required to move said closure element from said first position to said second position.

3. The valve of claim 2, wherein said adjustment means comprises a lid movably mounted on said housing, said closure element being mounted to said lid.

4. The valve of claim 1, wherein said closure element comprises diaphragm means.

5. The valve of claim 4, wherein said lid has an internal peripheral groove and said diaphragm means includes a peripheral bead edge portion positioned in said groove.

6. For use in a urine drainage device which includes a catheter insertable into a bladder and a collection bag in fluid communication with the catheter, a valve for bladder control adapted to be interposed in the fluid communication path between the catheter and the collection bag, said valve comprising:
   (i) a housing having an inlet adapted to communicate with the bladder, a sealing bead surrounding said inlet, and an outlet adapted to communicate with the collection bag;
   (ii) a closure element mounted to said housing and partially defining a chamber into which said outlet opens; and
   (iii) means for pulling said closure element taut over said inlet to resiliently seal said inlet from communicating with said chamber, said closure element being movable between a first position in which said closure element contacts said sealing bead to form a fluid tight seal and a second position in which said inlet and said outlet are in fluid communication through said chamber, wherein said closure element has a first fluid contacting surface area responsive to fluid pressure in the bladder when in said first position and a second fluid contacting surface area responsive to fluid pressure to the bladder when in said second position, said second fluid contacting surface area being substantially greater than said first fluid contacting surface area, such that the bladder fluid pressure required to maintain said closure element in said second position is substantially less than the bladder fluid pressure reguired to move said closure element from said first position to said second position.

7. The valve of claim 6, further comprising means to adjust the resiliency of said closure element to change the fluid pressure required to move said closure means from said first position to said second position.

8. The valve of claim 7, wherein said adjusting means comprises a lid movably mounted to said housing, said closure element being mounted to said lid.

9. For use in a urine drainage device which includes a catheter insertable into a bladder and a collection bag in fluid communication with the catheter, a valve for bladder control adapted to be interposed in the fluid communication path between the catheter and the collection bag, said valve comprising:
   a circular valve housing;
   an inlet centrally arranged in said housing and adapted to be connected to the catheter in fluid communication with the bladder;
   a sealing bead surrounding said inlet;
   an outlet adapted to be connected to the collection bag;
   a lid having an internal peripheral groove; and
   diaphragm means having a peripheral bead edge portion positioned to said groove;
   said lid mounting said diaphragm means to said housing such that said diaphragm means and said housing together define a chamber into which said outlet opens;
   said diaphragm means being pulled taut over said valve housing to resiliently contact said sealing bead and form a fluid tight seal preventing fluid communication between said inlet and said outlet when the fluid pressure in said inlet is below a predetermined pressure, said diaphragm means opening said inlet to communication with said outlet means through said chamber in response to a predetermined pressure in the bladder, a lower pressure in the bladder substantially below said predetermined pressure being capable of keeping the inlet open until the resilient sealing force acting on said diaphragm means exceeds the force acting on said diaphragm means due to said lower pressure in the bladder.

10. The valve of claim 9, further comprising means for adjustably mounting said lid to said housing to permit adjustment of the resiliency of said diaphragm means to thereby change the fluid pressure required to move said diaphragm means from said first position to said second position.

11. The valve of claim 10, wherein said valve housing includes peripheral screw threads, and said lid includes cooperating screw threads to permit said adjustment of the resiliency of said diaphragm means.

* * * * *